(12) United States Patent
Tracey et al.

(10) Patent No.: US 9,014,798 B2
(45) Date of Patent: Apr. 21, 2015

(54) AUTOMATED STIMULUS ARTIFACT REMOVAL FOR NERVE CONDUCTION STUDIES

(75) Inventors: Brian Tracey, Arlington, MA (US); Srivathsan Krishnamachari, Cambridge, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 1692 days.

(21) Appl. No.: 11/584,184

(22) Filed: Oct. 20, 2006

(65) Prior Publication Data

US 2007/0118047 A1 May 24, 2007

Related U.S. Application Data

(60) Provisional application No. 60/728,460, filed on Oct. 20, 2005.

(51) Int. Cl.
*A61B 5/04* (2006.01)
*A61B 5/00* (2006.01)

(52) U.S. Cl.
CPC ............ *A61B 5/04001* (2013.01); *A61B 5/7207* (2013.01); *A61B 5/72* (2013.01); *A61B 5/7203* (2013.01); *A61B 5/7217* (2013.01)

(58) Field of Classification Search
CPC ...... A61B 5/72; A61B 5/7203; A61B 5/7207; A61B 5/7217; A61B 5/04001
USPC ......... 600/544, 545, 546, 547, 554; 607/2, 48
See application file for complete search history.

(56) References Cited

U.S. PATENT DOCUMENTS

| | | | |
|---|---|---|---|
| 5,976,094 A | 11/1999 | Gozani | |
| 6,768,924 B2 | 7/2004 | Ding et al. | |
| 6,936,012 B2 | 8/2005 | Wells | |
| 6,944,502 B2 | 9/2005 | Charvin et al. | |
| 7,424,322 B2 | 9/2008 | Lombardi et al. | |
| 2005/0277844 A1* | 12/2005 | Strother et al. | 600/546 |
| 2006/0178706 A1 | 8/2006 | Lisogurski et al. | |
| 2006/0287609 A1* | 12/2006 | Litvak et al. | 600/554 |

OTHER PUBLICATIONS

Wagenaar, Daniel A and Steve M Potter. "Real-time multi-channel stimulus artifact suppression by local curve fitting." Journal of Neuroscience Methods. 120. 2002. p. 113-120.*
Wagenaar, Daniel A and Steve M Potter. "Real-time multi-channel stimulus artifact suppression by local curve fitting." Journal of Neuroscience Methods 120. 113-120. 2002.*
Gozani et al., Electrodiagnostic Automation: Principles and Practice, Phys Med Rehabil Clin N Am, 2005, 1015-1032, 16.
Grieve et al., Nonlinear Adaptive Filtering of Stimulus Artifact, IEEE Transactions on Biomedical Engineering, Mar. 2000, vol. 47, No. 3.

* cited by examiner

*Primary Examiner* — Adam Eiseman
(74) *Attorney, Agent, or Firm* — Pandiscio & Pandiscio

(57) ABSTRACT

A method for the automated removal of a stimulus artifact from an electrophysiological signal waveform, wherein the novel method comprises:
  providing a model of the stimulus artifact that is physically derived and is based on known properties of the electrophysiological signal waveform acquisition hardware and stimulator; and
  filtering the stimulus artifact out of the electrophysiological signal waveform using the model.

29 Claims, 15 Drawing Sheets a) NCS data collected with Device A b) Front-end circuitry of Device A a) NCS data collected with DEVICE_B b) Front-end circuitry of DEVICE_B a) Initial estimate of SA fit range b) Refined estimate after signal onset detection

AUTOMATED STIMULUS ARTIFACT REMOVAL FOR NERVE CONDUCTION STUDIES

REFERENCE TO PENDING PRIOR PATENT APPLICATION

This patent application claims benefit of pending prior U.S. Provisional Patent Application Ser. No. 60/728,460, filed Oct. 20, 2005 by Brian H. Tracey et al. for AUTOMATED STIMULUS ARTIFACT REMOVAL FOR NERVE CONDUCTION STUDIES, which patent application is hereby incorporated herein by reference.

FIELD OF THE INVENTION

This invention relates to apparatus and methods for the assessment of electrophysiological signals. More particularly, this invention relates to improving the accuracy of such electrophysiological assessment by automatically removing signal artifacts created by electrical stimulation. While the invention is generally applicable to a wide range of electrophysiological signals, it is focused on artifact removal for nerve conduction studies.

BACKGROUND OF THE INVENTION

In a variety of biomedical applications, an electrical stimulus is applied to tissue in order to evoke a desired response. Examples of such electrical stimulus can be found in cardiac, evoked potential, and nerve testing applications. The stimulus can cause unwanted artifacts that can complicate the interpretation of recorded signals. This patent application describes a technique for removing these artifacts, focusing on application to the field of nerve conduction testing.

Nerve conduction studies (NCS) provide a reliable, accurate and sensitive means for detecting a variety of peripheral nervous system disorders. In NCS testing, a set of surface electrodes is placed against the skin overlying a nerve and a brief electrical stimulus is applied. If the electrical stimulus is of sufficient magnitude, it triggers a wave of membrane depolarization that spreads bi-directionally outward from the stimulus site. This wave of membrane depolarization can be detected with surface electrodes placed over the nerve at a site remote from the original stimulus site. For sensory nerves, this membrane depolarization signal is commonly referred to as a compound sensory nerve action potential (SNAP). This SNAP signal may be measured and analyzed. For motor nerves, the wave of membrane depolarization terminates at a neuromuscular junction (i.e., the motor endplate zone), causing depolarization of the muscle membranes and a resultant muscle contraction. In motor NCS, this response evoked in the muscle, which is generally referred to as a compound motor action potential (CMAP), is measured and analyzed.

NCS results are interpreted by comparing the patient's response characteristics to a normative reference that describes the range of values expected for healthy individuals. Prolongation of motor or sensory latencies can indicate nerve compression with injury to the nerve's myelin sheath, as can be seen in carpal tunnel syndrome (i.e., median nerve entrapment at the wrist) or ulnar neuropathy at the elbow. The CMAP and SNAP amplitudes are also clinically significant parameters. For example, low sural nerve SNAP amplitude is a reliable, accurate and sensitive indicator of polyneuropathy in diabetic patients.

The accuracy with which response parameters are measured critically influences NCS clinical utility. Unreliable parameter estimates' reduce NCS accuracy and may even lead to incorrect diagnoses.

A common problem in NCS is that a stimulus artifact (SA) can distort the nerve signal. This is particularly true for sensory studies (as compared to motor studies) inasmuch as sensory signals are smaller in amplitude and therefore may be more easily distorted. Several mechanisms can give rise to SA, but the stimulus artifact is generally the result of residual stimulus current spreading through the body tissue. The degree of SA observed in a test depends on the properties of the patient's skin, and the skin-electrode interface, among other parameters.

There are many clinical and non-clinical situations that call for rapid, reliable and low-cost NCS testing. Reliable automated devices have been introduced into the marketplace to assess neuromuscular function in primary care physician and small clinic settings. These automated NCS devices are designed to be used by personnel without specialized training. The apparatus and method described by Gozani in U.S. Pat. No. 5,976,094 is one such example of a device and method that is successfully used to make neuromuscular assessments of peripheral nerves many thousands of times every year. With the Gozani method and device, an NCS signal is evoked, recorded and analyzed by the device and the results are provided to the user. While automated NCS devices have proven highly successful in clinical applications, it is recognized that the removal or minimizing of stimulus artifacts would further improve the performance of the devices. For automated testing, it is necessary to minimize or remove the stimulus artifact in a manner which does not require significant user training or interaction.

Significant efforts have been made to remove or minimize stimulus artifacts in bioelectrical signals such as NCS.

The stimulus artifact is most easily handled when it does not overlap in time with the signal of interest. U.S. Pat. No. 6,768,924 and U.S. Patent Publication No. 2006/0173496 both teach methods for identifying and zeroing out segments of a bioelectrical signal that contains SA. These documents provide examples of a technique denoted as "hardware blanking", a term which is used below. Others have proposed a software-based approach for accomplishing the same goal. All of these approaches are based on the concept of separating the stimulator and detector electrodes by a distance sufficient to time-separate the SA and the signal of interest. However, for NCS, the possible electrode sites are frequently constrained by anatomy. Thus, it is not always possible to separate the stimulator and detector electrodes by a distance sufficient to ensure that the signal of interest arrives after the stimulus artifact has decayed away.

In clinical practice, stimulus artifacts in NCS studies are often minimized by rotating the orientation of the stimulation electrodes. This approach has the effect of changing the electrical fields at the detector electrodes. It is often possible to find an electrode orientation which adequately stimulates the nerve but minimizes the stimulus artifact. The primary disadvantage of this approach is that it requires a highly skilled specialist to perform the NCS test. This is contrary to the goal of automated NCS testing, which seeks to use automated NCS test devices which require minimal user training and interaction.

Several patents teach related methods for reducing SA via electrode placement. U.S. Pat. No. 6,944,502 teaches a method for reducing SA in the measurements of auditory evoked potential by placing the detector electrodes perpendicular to the stimulator electrodes. However, this approach is not practical for NCS applications, since the anatomical differences between patients mean that a single electrode geometry will not be optimal for all patients. U.S. Patent Publication No. 2006/178706 teaches that SA may be reduced in ECG recordings by deploying multiple electrode pairs, and then choosing the electrode pair that minimizes SA. However, this approach generally requires more complicated sensors and data acquisition systems, and would increase the cost of an NCS study.

In another approach, adaptive signal processing methods are used to cancel SA based on information provided by a reference channel. This reference channel provides a measurement of the SA but should not contain any data from the signal of interest. The reference channel may be obtained by using off-nerve measurements, or by using stimuli that are low enough that no nerve response is triggered (see U.S. Pat. No. 6,936,012). Unfortunately, the usefulness of adaptive approaches may be limited, because a good reference channel may not be available (i.e., the reference channel may be contaminated by the signal of interest, or the SA in the reference channel may have a different morphology than that in the primary channel, or both). In addition, recording a reference channel increases hardware requirements and drives up the cost and complexity of NCS equipment.

Another class of signal processing methods involves modeling the stimulus artifact by fitting polynomials, splines, or exponential curves to the data. These shapes are empirically determined by the algorithm designer, and are not linked to physical parameters of the electronics or the stimulus. Once the estimated stimulus artifact has been determined by this modeling, it is subtracted from the data. While this type of approach has merit, it can be difficult to find simple shapes that can account for the SA morphology throughout the full NCS waveform. Thus, some researchers have reverted to piecewise curve fits. However, such piecewise curve fitting generally complicates the curve fitting procedure and can actually make it more prone to error.

The electronics of the automated NCS device can have a significant impact in shaping the SA morphology. In principle, the shaping of SA introduced by the electronics can be removed using deconvolution. However, as is known to those skilled in the art, waveform reconstruction using deconvolution is subject to errors when the input data is noisy. Thus, it has been suggested that extensive waveform averaging can be used to reduce noise prior to deconvolution. However, in the NCS application, such waveform averaging would require patients to receive additional electrical shocks, making NCS studies longer and less comfortable for the patients.

SUMMARY OF THE INVENTION

The present invention provides a novel method and apparatus for stimulus artifact removal for automated NCS testing which can be done by personnel without specialized training. While the discussion below often refers to sensory (SNAP) signals, the present invention is applicable to both sensory (SNAP) and motor (CMAP) recordings. The present invention may also be applied to other electrophysiological recordings where stimulus artifact is present. The novel method and apparatus are robust enough to handle the most problematic cases of SA contamination, i.e., those in which the SA and the signal of interest are overlapped in time as well as in frequency. The novel method and apparatus are also robust enough to operate on potentially noisy data (from either sensory or motor NCS tests) that are collected using minimal waveform averaging, and do not pose additional hardware requirements such as the use of a reference channel.

The novel method for the automated removal of stimulus artifact described here makes use of a model for the SA that is physically derived and is based on known properties of the acquisition hardware and stimulator. This model is valid for the entire length of data capture and can be used to remove SA which is overlapped with the signal of interest. The invention also includes procedures for identifying which time periods should be used to fit the SA model, and for automatically judging the goodness-of-fit of the modeled SA.

In a preferred form of the invention, the method comprises the steps of:

(1) developing a model of the entire stimulus artifact based on physical mechanisms of the stimulus and hardware;

(2) determining whether SA removal should be attempted for a given trace;

(3) identifying a time period which can be used to estimate the model parameters, during which SA is present but no nerve signals are present;

(4) estimating model parameters by numerically fitting the SA model to the data identified in step 3 above;

(5) determining the goodness-of-fit for the modeled stimulus artifact;

(6) subtracting the modeled SA from the entire waveform, including the time period when the signal of interest is present; and (7) combining SA model fitting results across multiple acquired waveforms.

These seven steps, also sometimes referred to herein as procedures, will now be discussed in further detail.

(1) The development of an accurate model for the stimulus artifact is an important first step in the new method. In the preferred embodiment, the SA model is developed subject to certain criteria. First, the SA model assumes functional forms for the voltage established on the patient's skin by the stimulus. These functional forms are based on an understanding of the device behavior and electrode-skin interface. Thus, in one preferred embodiment, the voltage established on the skin of the patient is modeled as a decaying exponential voltage, due to the tail of the stimulus current. In another preferred embodiment, the voltage established on the skin of the patient is modeled with two components: a decaying exponential voltage, and a voltage step caused by a shift in the reference voltage. Second, all of the relevant characteristics of the data acquisition and processing electronics (such as analog filtering, digital filtering, and switching) are captured in the SA model. Finally, since SA may persist for a significant period of time and overlap the signal of interest, the SA shape is predicted throughout the entire time period of data capture. The final result is a model of SA that includes both known parameters (such as those describing the electronics of the NCS testing device) and unknown parameters (such as those describing the amplitudes, etc. of the voltages present on the skin).

(2) Next, a procedure is provided for determining whether (or not) SA removal should be attempted when processing a particular NCS waveform. The procedure may be as simple as detecting SA by comparing the peak amplitude in the likely SA region to a threshold, and then determining whether (or not) to remove the SA. This embodiment of the procedure, as well as more sophisticated embodiments of the procedure, are provided below.

(3) Assuming that SA removal is indicated, the next step is to determine which portion of the data should be used to estimate the unknown parameters of the SA model. A procedure is provided for finding a segment of the signal which contains the SA but not the signal of interest (i.e., the SNAP or CMAP signals). This portion of the data is sometimes referred to below as the "fit region". An initial estimate of the fit region is made based on clinical experience and the waveform features. This initial estimate must then be refined so as to ensure that it does not include any segments where the signal of interest is present, or where the signal of interest was clipped (e.g, such as where the NCS signal exceeded the input range of the A/D converter of the NCS testing device) during data acquisition. A preferred procedure searches for the NCS signal onset using separate algorithms for upward- or downward-deflected SA. The signal onset is detected based on changes in waveform slope and other features. In an alternate procedure, a matched filter (or other signal detection triggers) may be used to determine NCS signal onset. Once the NCS signal onset is determined, the SA "fit region" is adjusted so that it does not contain segments where the signal of interest is present. In a similar manner, the procedure provides for searching the data to identify clipped segments. Once identified, these clipped segments are excluded from the SA fit region.

(4) Next, a procedure is provided for estimating SA model parameters from the data values in the fit region. This procedure can use any of several numerical techniques for parameter estimation (e.g., optimized numerical solvers, brute-force solvers, look-up table approximations, etc.). This procedure may be extended to enforce additional constraints on the solution outside the SA fit region. For example, in one embodiment, the estimated SA waveform is required to meet specified constraints late in time as well as providing the best possible fit in the SA fit region. This particular embodiment can be useful to avoid "over-fitting" the model to the data from the identified SA fit region.

(5) After the SA model parameters have been estimated, the estimated SA waveform can be calculated and then compared to the raw data in order to determine whether a good fit has been achieved. This step is an important aspect of performing SA removal as part of an automated NCS test. Several embodiments of the goodness-of-fit procedures are described below. These goodness-of-fit tests generally involve calculating a metric and then comparing that metric to a threshold in order to determine if the fit is acceptable. In general, multiple metrics are tested, and all must be acceptable in order for the fit to be judged good. Possible metrics include (a) normalized squared error in the SA fit region; (b) worst-case error in the SA fit region; (c) metrics such as the Durbin-Watson or "runs" statistic, that seek to discover correlated trends in the error; and (d) constraints on the fit for other portions of the data recording. An example of the aforementioned metric (d) might be checking the relationship between the SA model and the data at times after the end of the nerve signal.

(6) The last step in processing the NCS waveform is subtracting the estimated SA waveform from the raw data waveform, once the determination has been made that the SA fit is good. The corrected waveform (i.e., the waveform remaining after the estimated SA waveform has been removed from the NCS raw data waveform) is used for clinical analysis and data display.

(7) Finally, the invention also provides a procedure for combining information across multiple waveforms. In one embodiment, in addition to seeking good correspondence between the SA model and the data, good correspondence is also sought between the SA model and other waveforms acquired with similar stimulus parameters. This procedure seeks to minimize the possibility that insufficiently-corrected data will be accepted for clinical analysis. Other embodiments of this procedure are outlined below.

The invention will be further understood upon consideration of the following drawings, description, and claims.

In one form of the present invention, there is provided a method for the automated removal of a stimulus artifact from an NCS signal waveform, wherein the novel method comprises the procedure steps of:

(1) developing a model of the stimulus artifact based on physical mechanisms of the NCS stimulus and NCS hardware;

(2) determining whether stimulus artifact removal should be attempted for a given NCS signal waveform;

(3) identifying a time period which can be used to estimate the model parameters, during which the stimulus artifact is present but no signals of interest are present, whereby to define a fit region within the NCS signal waveform;

(4) estimating model parameters by numerically fitting the stimulus artifact model to the data within the fit region;

(5) determining the goodness-of-fit for the modeled stimulus artifact; and (6) subtracting the modeled stimulus artifact from the NCS signal waveform, including the time period when the signal of interest is present.

In another form of the present invention, there is provided a method for the automated removal of a stimulus artifact from an NCS signal waveform, wherein the novel method comprises:

providing a model of the stimulus artifact that is physically derived and is based on known properties of the NCS signal waveform acquisition hardware and stimulator; and filtering the stimulus artifact out of the NCS signal waveform using the model.

In another form of the present invention, there is provided a method for the automated removal of a stimulus artifact from an NCS signal waveform, wherein the novel method comprises the procedure steps of:

(1) developing a model of the stimulus artifact based on physical mechanisms of the NCS stimulus and NCS hardware;

(2) identifying a time period which can be used to estimate the model parameters, during which the stimulus artifact is present but no signals of interest are present, whereby to define a fit region within the NCS signal waveform;

(3) estimating model parameters by numerically fitting the stimulus artifact model to the data within the fit region;

(4) determining the goodness-of-fit for the modeled stimulus artifact; and (5) subtracting the modeled stimulus artifact from the NCS signal waveform, including the time period when the signal of interest is present.

In another form of the present invention, there is provided a method for the automated removal of a stimulus artifact from an electrophysiological signal waveform, wherein the novel method comprises the procedure steps of:

(1) developing a model of the stimulus artifact based on physical mechanisms of the electrophysiological stimulus and electrophysiological hardware;

(2) identifying a time period which can be used to estimate the model parameters, during which the stimulus artifact is present but no signals of interest are present, whereby to define a fit region within the electrophysiological signal waveform;

(3) estimating model parameters by numerically fitting the stimulus artifact model to the data within the fit region;

(4) determining the goodness-of-fit for the modeled stimulus artifact; and (5) subtracting the modeled stimulus artifact from the electrophysiological signal waveform, including the time period when the signal of interest is present.

In another form of the present invention, there is provided a method for the automated removal of a stimulus artifact from an electrophysiological signal waveform, wherein the novel method comprises:

providing a model of the stimulus artifact that is physically derived and is based on known properties of the electrophysiological signal waveform acquisition hardware and stimulator; and filtering the stimulus artifact out of the electrophysiological signal waveform using the model.

In another form of the present invention, there is provided an apparatus for the automated removal of a stimulus artifact from an electrophysiological signal waveform, wherein the novel apparatus comprises:

(1) a model of the stimulus artifact based on physical mechanisms of the electrophysiological stimulus and electrophysiological hardware;

(2) apparatus for identifying a time period which can be used to estimate the model parameters, during which the stimulus artifact is present but no signals of interest are present, whereby to define a fit region within the electrophysiological signal waveform;

(3) apparatus for estimating model parameters by numerically fitting the stimulus artifact model to the data within the fit region;

(4) apparatus for determining the goodness-of-fit for the modeled stimulus artifact; and (5) apparatus for subtracting the modeled stimulus artifact from the electrophysiological signal waveform, including the time period when the signal of interest is present.

In another form of the present invention, there is provided an apparatus for the automated removal of a stimulus artifact from an electrophysiological signal waveform, wherein the novel apparatus comprises:

a model of the stimulus artifact that is physically derived and is based on known properties of the electrophysiological signal waveform acquisition hardware and stimulator; and apparatus for filtering the stimulus artifact out of the electrophysiological signal waveform using the model.

DETAILED DESCRIPTION OF THE INVENTION

Figure 1:
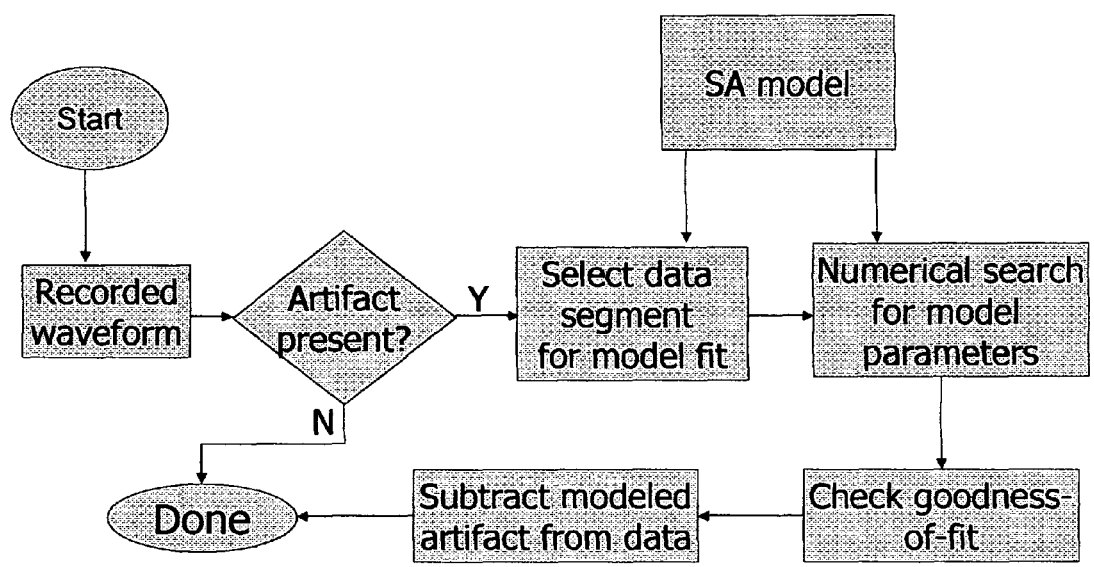
FIG. 1 illustrates a top-level flowchart of the procedures used to effect SA removal from a single trace, i.e., the aforementioned procedures (1)-(6), in accordance with one form of the invention;.

The present invention comprises a novel method and apparatus for automated stimulus artifact removal for automated NCS testing. The aforementioned procedures (1)-(6) relate to SA removal from a single waveform. FIG. 1 shows a high-level flowchart illustrating a preferred embodiment of these procedures (1)-(6). These procedures (1)-(6) will be discussed in order, followed by a description of procedure (7), which relates to combining information across multiple waveforms.

Figure 2:
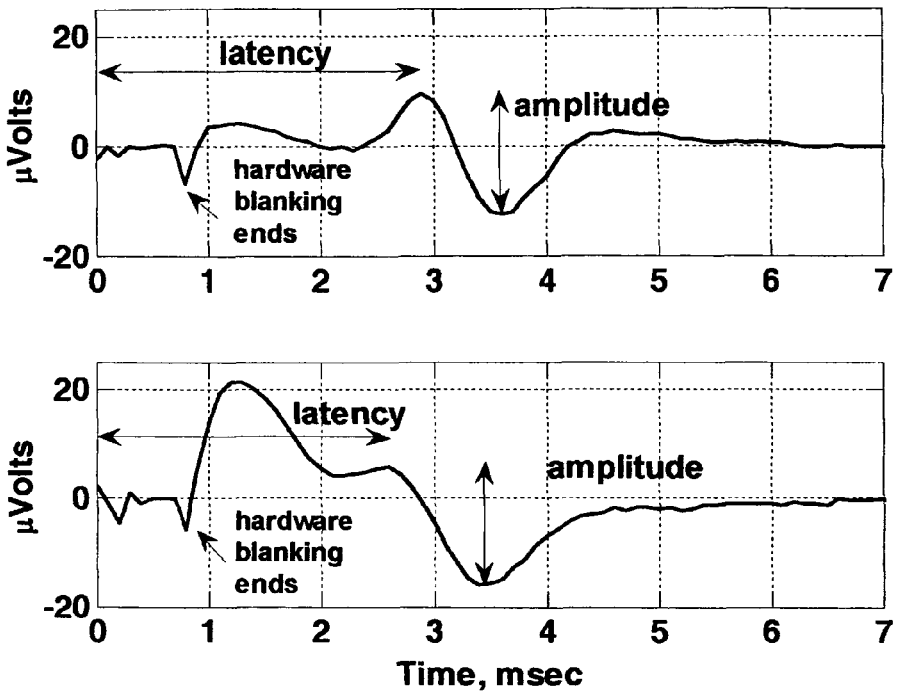
FIG. 2A shows examples of stimulus artifacts collected during NCS sensory studies using a device denoted as Device A—the top panel shows a case in which SA does not overlap the SNAP signal, while the bottom panel shows a case in which SA overlaps and distorts the SNAP signal.
FIG. 2B shows a simplified circuit diagram for the data acquisition electronics of Device A.
Figure 2:
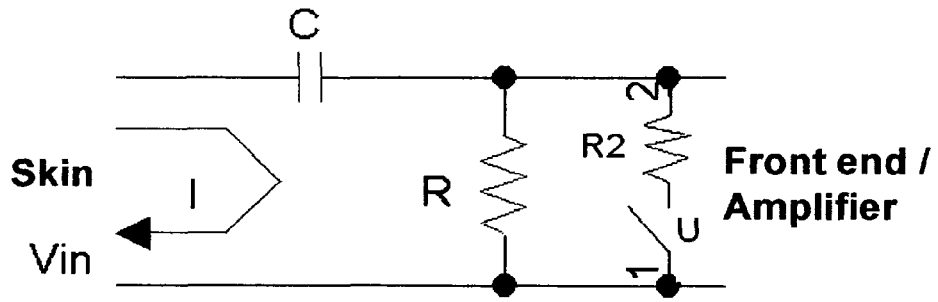
Figure 3:
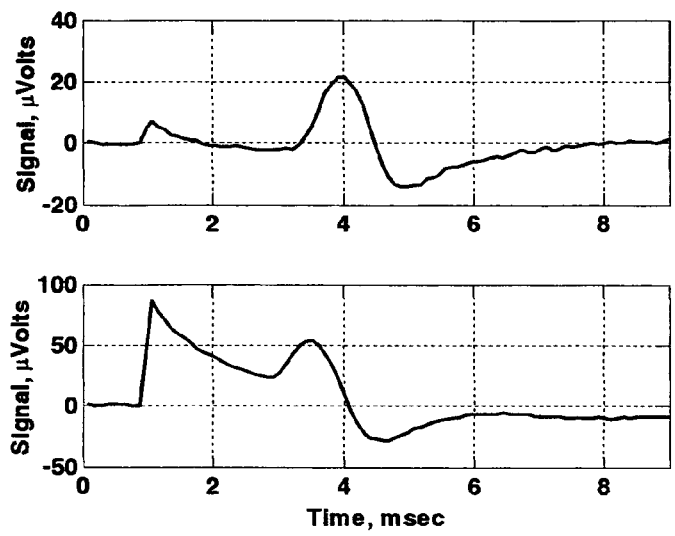
FIG. 3A shows examples of stimulus artifacts collected during NCS sensory studies using a device denoted as Device B—the top panel shows a case in which SA does not overlap the SNAP signal, while the bottom panel shows a case in which SA overlaps and distorts the SNAP signal.
FIG. 3B shows a simplified circuit diagram for the data acquisition electronics of Device B—FIGS. 2 and 3, when taken together, illustrate that the electronics of the NCS test device have a profound effect on the shape of the stimulus artifact.
Figure 3:
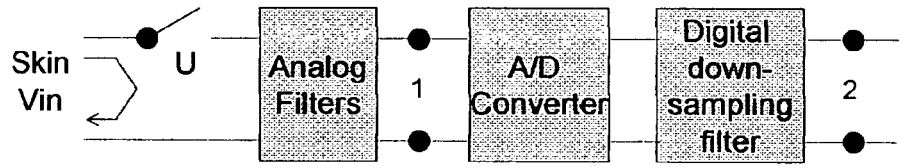

As a preface to the discussion, FIGS. 2 and 3 show example waveforms from sensory nerve NCS studies where stimulus artifact is present. The data in FIG. 2 is collected from an NCS device denoted as Device A. In many cases, as in the upper panel of FIG. 2A, the SA decays away before the signal of interest arrives. In other cases, as seen in the lower panel of FIG. 2A, SA distorts the apparent amplitude of the signal of interest (in this case, a SNAP signal). The distorted amplitude value can affect the interpretation of NCS results or potentially lead to mis-diagnosis.

The data in FIG. 3 was collected using a second NCS device, denoted as Device B. Device A and Device B differ in terms of the front-end electronics used to filter and amplify the signal. Taken together, FIGS. 2 and 3 illustrate that changes in the electronics of the NCS test device can have a very significant effect on the morphology of the stimulus artifact.

(1) Stimulus Artifact Modeling

Figure 4:
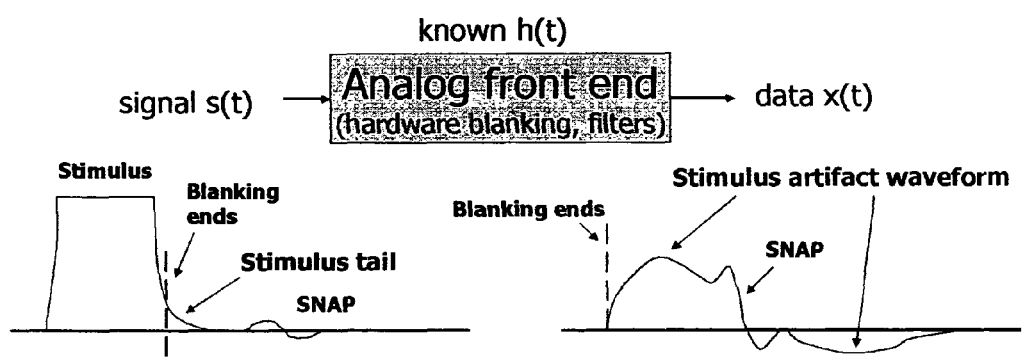
FIG. 4 illustrates (in "cartoon" form) how the voltage established on the skin of the patient is filtered by the device electronics to produce the recorded SA.

The development of an accurate SA model is an important step in SA removal. FIG. 4 shows a "cartoon" view of the elements that should be included in the model. The constant-current NCS stimulus creates a high voltage on the patient's skin (left side of the figure). Hardware blanking may be used to shield the electronics of the NCS testing device during application of the stimulus to the patient. However, residual stimulus-generated voltages can persist on the patient's skin after hardware blanking ends. These voltages are then filtered and shaped by the electronics which have a known impulse response h(t). This gives rise to an SA waveform in the recorded data that differs from the SA waveform present on the skin (right side of figure).

The first step in the modeling procedure is to determine a set of physically reasonable voltage waveforms that may exist on the patient's skin. These may include decaying exponential terms, voltage steps, and other terms. In deciding what terms to model, use may be made of experimental measurements that clarify the phenomena which gives rise to SA. Alternatively, a simple model may be adopted initially, and additional terms added thereafter, until the performance of the entire SA removal process, i.e., the aforementioned procedures (1)-(6), is satisfactory.

In a second step in the modeling procedure, a calculation is made of the response of the front-end electronics to the voltage waveforms that are assumed to be present on the skin. The relevant features of the front-end electronics are modeled, including hardware blanking mechanisms, analog filters, and front-end capacitance. Any digital filtering that affects the acquired data (for example, digital anti-aliasing or downsampling filters) is also modeled. The result is a physically-based SA model that contains a small number of unknown parameters.

(1A) Embodiment of SA Model for Device A

As a first example, an embodiment of the SA model for Device A is considered. FIG. 2 shows a circuit diagram for the first stage of the analog front end. A second high-pass RC filter (not shown) follows the circuit shown in FIG. 2. During and just after delivery of the stimulus, a blanking switch U is closed. This causes current to flow through a low-impedance shunt path, shielding the analog front end from the stimulus. After a fixed time, the blanking switch is opened and the circuit functions as a high-pass filter. The capacitor C can accumulate a charge prior to the switch opening. When the switch is opened, the capacitor discharges into the front end. At the same time, residual stimulus currents on the skin are measured by the recording electrodes. These two voltage sources create the characteristic rising-and-falling shape seen in the NCS signal between 1-2 msec in FIG. 2.

A model of the stimulus artifact is derived by assuming that the input voltage (i.e., the voltage input to the detector electrode) causing the SA is a decaying exponential waveform with unknown amplitude and decay constant. This is written as:

$$v_{exp}(t) = A e^{-t/\tau} u(t - t_{blankingEnd}) \quad (1)$$

where A and τ are the unknown amplitude and time constant of the input exponential, and u is a unit step function. The notation indicates that the step change occurs after the hardware blanking ends, at time $t_{blankingEnd}$. The response of the acquisition system to this input voltage can be calculated. The response of the two high-pass filter stages (taking into account the initial charge on the capacitor) is found to be $$f(t) = A \left( \frac{-1/\tau}{1 - \frac{RC}{\tau}} \right) \quad (2)$$

-continued $$\left( \frac{e^{-t/RC}}{(1/RC - 1/\tau)} + \frac{te^{-t/RC}}{RC/\tau} - \frac{e^{-t/\tau}}{(1/RC - 1/\tau)} \right) u(t - t_{blankingEnd})$$

where RC is the time constant of a single high-pass filter. Note from Equation 2 that the analog front-end transforms the exponential input into an SA which grows initially, then decays over time.

Figure 5:
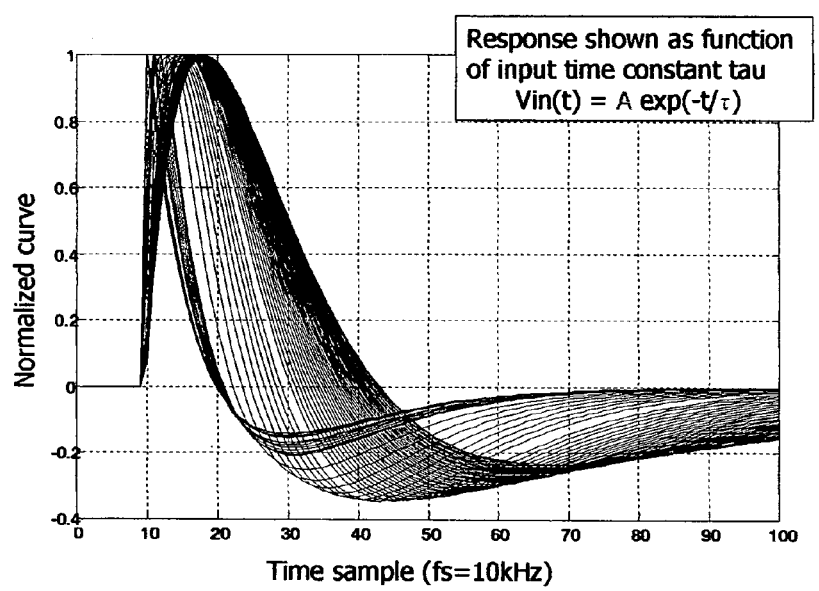
FIG. 5 illustrates the family of stimulus artifact curves that are predicted for Device A—this provides a first example of the procedure for modeling the stimulus artifact.

FIG. 5 shows a family of curves generated from Equation 2. Note that the shape of the SA depends heavily on the time constant τ. For small time constants, the SA drops off rapidly but, for larger values, the SA may have a noticeable amplitude throughout much of the data capture. Also note that the peak of the SA waveform for Device A is a function of the time constant, a fact that will be exploited below.

1B. Embodiment of SA Model for Device B

The lower panel of FIG. 3 shows a schematic view of the front-end electronics for Device B. Several reference points ("1" and "2") are also shown.

As with Device A, SA for Device B is assumed to be due (at least in part) to voltages on the skin that can be represented by decaying exponentials. A second effect can be important for Device B. More particularly, in Device B, hardware blanking is provided by a switch that fully disconnects the analog front end from the input voltage (i.e., the voltage which is the input to the detector electrode). Thus, there is a possibility that a DC voltage shift on the skin will occur during the blanking period. When the blanking switch closes, this shift manifests itself as a step function.

Thus, for Device B, the voltage on the skin (i.e., the input to the electronics) is modeled with two terms:

$$v_{exp}(t) = A e^{-t/\tau} u(t - t_{blankingEnd}) \quad (3)$$

$$v_{dc}(t) = B u(t - t_{blankingEnd})$$

In these equations, A and τ are the amplitude and time constant of the decaying exponential, B is the amplitude of the DC voltage shift, and u is a unit step function. The notation indicates that the step change occurs after the hardware blanking ends, at time $t_{blankingEnd}$.

The response of the electronics to these input voltages is now calculated. The signals first pass through two single-pole RC high-pass filters (and also a low-pass filter which does not appreciably affect the response). Thus, at point "1" in the circuit, the response to the exponential input Vexp(t) is:

$$\tilde{f}_{exp}(t) = A[g_1(t)e^{-t/\tau} + g_2(t)e^{-t/RC}]u(t - t_{blankingEnd}) \quad (4)$$

where $$g_1(t) = \left(1 - \frac{1/RC}{1/RC - 1/\tau}\right)^2$$

and $$g_2(t) = \left(\frac{1/RC}{1/RC - 1/\tau}\right)\left[2 - \frac{t}{RC} - \frac{1}{RC(1/RC - 1/\tau)}\right].$$

The response to the step voltage shift input is:

$$\tilde{f}_{dc}(t) = B e^{-t/RC}[1 - t/RC] u(t - t_{blankingEnd}) \quad (5)$$

Finally, the signal is digitized and downsampled. As part of this process, the signal is filtered using a digital filter. The SA removal algorithm only has access to this digitally filtered waveform, so digital filtering effects must be included in the SA model. In FIG. 3, the digitally filtered waveform is shown at tap point "2" in the circuit drawing.

In one embodiment, the digital filtering consists of a finite impulse response (non-recursive) filter. Given a digitized time series x[n], the filter output is given by:

$$y[n] = \sum_{m=-N}^{N} b[m]x[n-m] \quad (6)$$

where b[m] are the digital filter coefficients. Note that because the filter is applied in a block processing mode, the filtering is centered in time around the current time sample to avoid introducing an overall time delay.

The effects of the digital filter on SA can be exactly modeled by simply applying the same filter coefficients to the SA model output:

$$f_{exp}[n] = \sum_{m=1}^{M} b[m]\tilde{f}_{exp}[n-m] \quad (7)$$

$$f_{dc}[n] = \sum_{m=1}^{M} b[m]\tilde{f}_{dc}[n-m] \quad (8)$$

Figure 6:
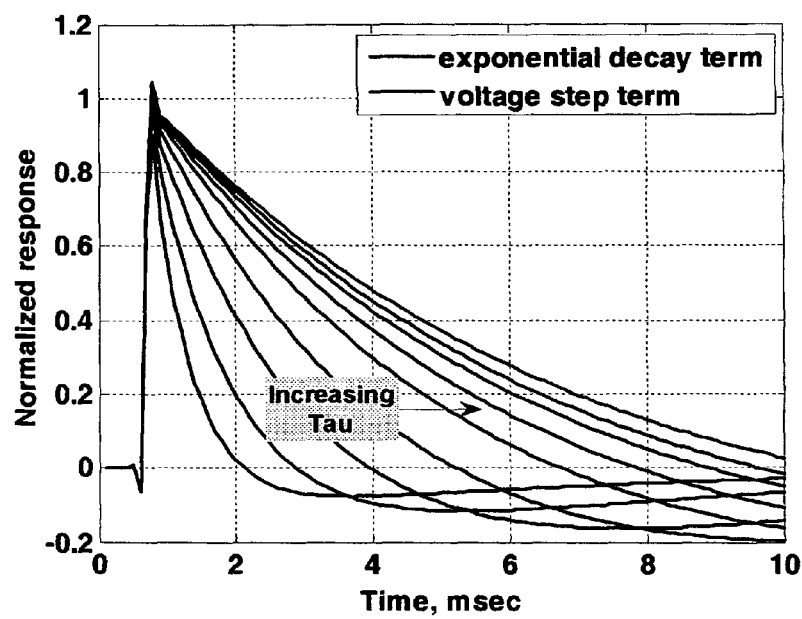
FIG. 6 illustrates the family of stimulus artifact curves that are predicted for Device B (for this device, several different phenomena are expected to give rise to stimulus artifact)—this provides a second example of the procedure for modeling the stimulus artifact.

FIG. 6 shows a family of unit-amplitude curves (i.e., A=B=1) generated from the equations above. The response to exponential input, $f_{exp}$, is shown as a function of the time constant. The response to DC shift, $f_{dc}$, has a constant shape. The digital filtering affects the shape of the rapid rise which is observed after hardware blanking ends (FIG. 3A).

(2) Determining Whether to Attempt SA Removal for a Given Waveform

The present invention also provides a procedure for determining whether SA removal should be attempted for a given waveform. The principal step in this procedure is applying a test to the data to determine if significant SA is present in the waveform. Additional tests may be applied to determine if SA removal is worthwhile and/or likely to succeed. These tests can help to reduce computational load on the device by avoiding unneeded SA fitting.

Figure 7:
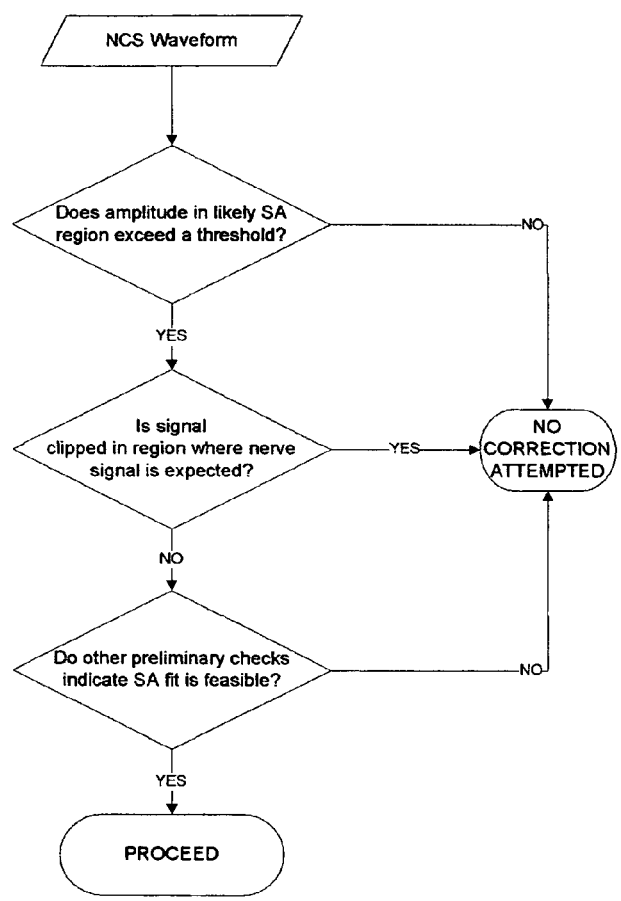
FIG. 7 illustrates an embodiment of the procedure for determining whether SA removal should be attempted.

FIG. 7 shows a preferred embodiment of this procedure. In this embodiment, an amplitude test is used to determine whether SA is present or not. Based on clinical experience, the time period most likely to include SA is identified. The maximum amplitude of the rectified (absolute value) signal in this time period is then compared to a threshold level to determine if SA is present on the trace.

FIG. 7 includes two additional tests. First, a test is made to see if the signal is clipped during time periods when nerve signals are expected. If so, the waveform presumably does not contain useful information, and SA removal is not needed. Second, features of the waveform are analyzed to determine if the SA shape is similar to that expected by the SA model. If it is clearly dissimilar, SA removal will generally fail and there is no purpose in running the algorithm.

Other embodiments are possible in which the amplitude test for detecting SA is replaced by other SA detectors. These may include matched filters for the SA shape, other morphology-based detectors, energy detectors that seek to identify activity in the frequency bands where SA is concentrated, etc.

(3) Determination of the Data Samples to be Used in Estimating the Parameters of the Stimulus Artifact Model Since the parameters of the SA model must be estimated from the NCS data, it is important to find a section of the waveform that contains SA waveform features but no nerve signal. This can be considered as a segmentation problem in which an SA segment is identified. This SA segment is sometimes denoted herein as the "fit region" (see below).

Figure 8:
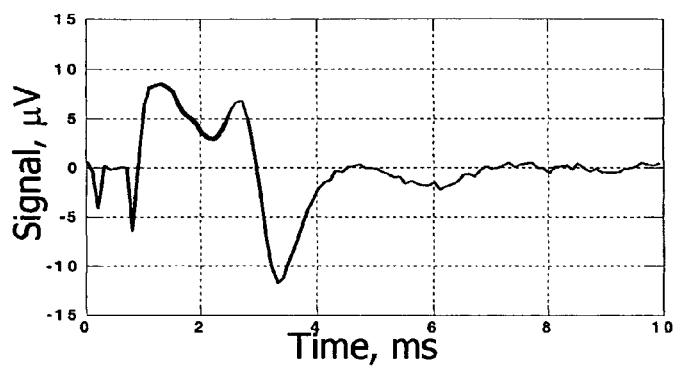
FIG. 8 shows an example of applying the segmentation procedure to data acquired using Device A, with FIG. 8A showing the initial estimate of the SA fit range, and FIG. 8B showing the refined estimate after signal onset detection.
Figure 8:
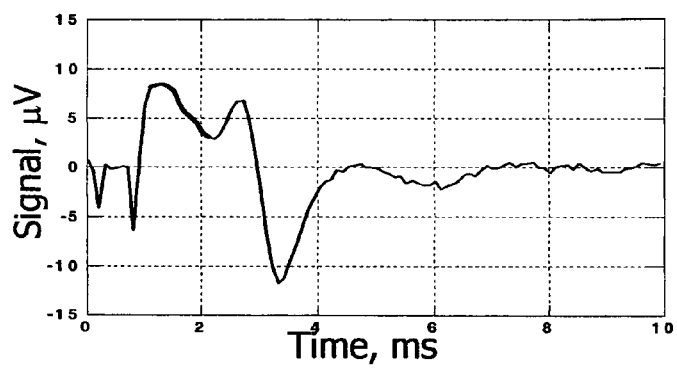

FIG. 8 shows a flowchart of an embodiment of this procedure. In the first step, an initial estimate of the fit region is made. In the remaining steps, this estimate is refined so as to ensure that it does not contain the nerve signal of interest or clipped regions of the signal. FIG. 8 shows an example waveform (from Device A) with the initial (FIG. 8A) and refined (FIG. 8B) estimates of the fit region.

(3A) Initial Fit Region Estimate (3Ai) Embodiment of the Procedure for Device A

FIG. 4 shows that, for Device A, the peak of the SA waveform is a function of the time constant. This fact can be useful in setting the initial fit region estimate.

More particularly, this embodiment makes use of a look-up table which describes the predicted shape of the baseline curve. The shape is determined by a single parameter, the input time constant τ, as is plotted in FIG. 5. A look-up table was generated which contains three values for each input time constant value. These are (a) the time at which the baseline first reaches 90% of the peak value; (b) the time at which the baseline peaks; and (c) the time (after peaking) at which the baseline falls to 10% of the peak value. These three values can be denoted as $T_{Lo90}(\tau)$, $T_{Peak}(\tau)$ and $T_{Hi10}(\tau)$, respectively, and are tabulated as functions of the input time constant τ.

First, the location of the baseline peak is estimated. The range of possible peak locations is set to start shortly after the end of hardware blanking, and to end at the latest peak location that can be predicted by the baseline model (for Device A, these bounds translate into the range 1.2-1.9 msec). If the data are unclipped, the sample with maximum amplitude in this region is taken to be the baseline peak. If the data are clipped, the median sample of the clipped region (rounded down) is taken to be the peak.

Next, the estimated peak location is used to set an initial fit range. Because the SA peak is a function of the input time constant, the estimated peak and the look-up table are used to find an initial estimate of the input time constant, τ'. The fit region is set to run from $T_{Lo90}(\tau')$ to $T_{Hi10}(\tau')$. This intentionally emphasizes fitting the baseline after the peak. The nerve signal of interest comes after the baseline peak, so accuracy during this part of the waveform is most important.

(3Aii) Embodiment of the Procedure for Device B

For Device B, the peak of SA occurs immediately after hardware blanking ends. Thus, for Device B, the initial fit region is set to run from just after the end of hardware blanking to a fixed end time. This fixed end time represents a time by which a large majority of the SA waveforms are expected to have decayed significantly.

(3B) Refinement to Avoid Clipped Data and the Signal of Interest

Section 3A above discussed the first processing step from FIG. 8. The remaining steps are discussed here. Their embodiments are identical for Device A and Device B.

First, any clipped data samples in the SA fit region are identified by checking the A/D values. The list of clipped samples is stored for later processing.

Figure 9:
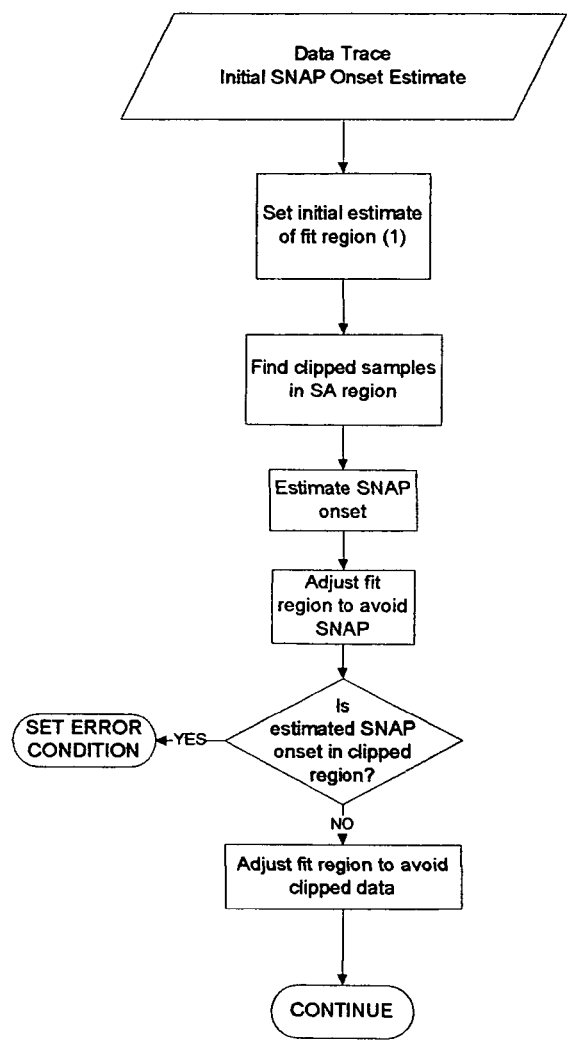
FIG. 9 illustrates an embodiment of the segmentation procedure that chooses which data samples will be used for fitting the stimulus artifact model.
Figure 10:
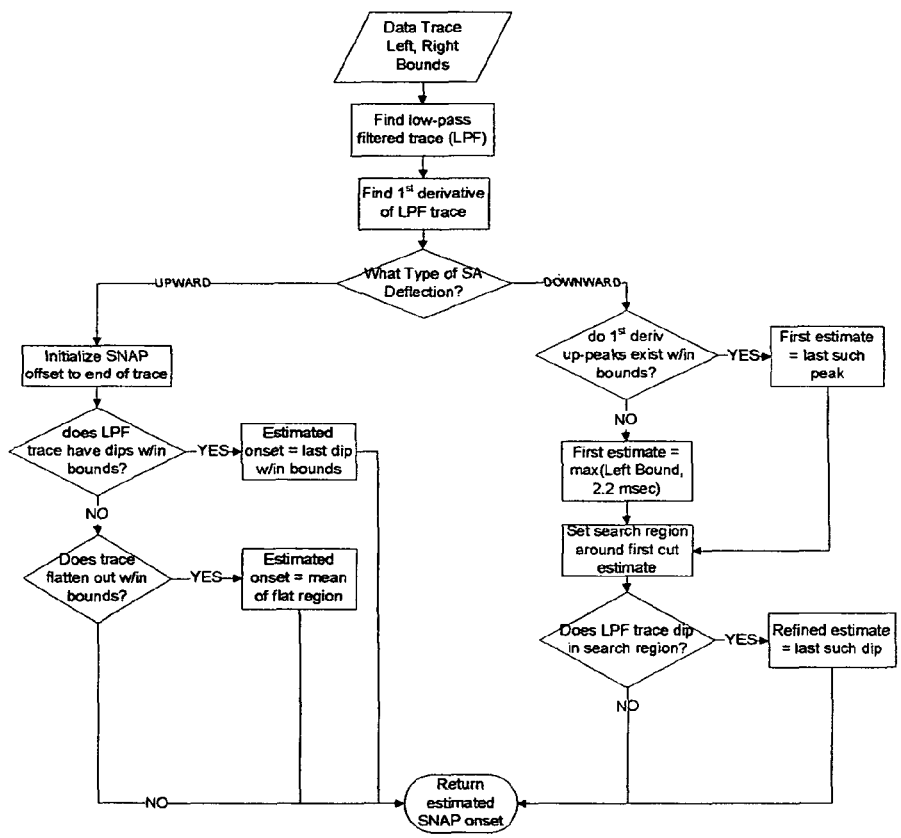
FIG. 10 shows further details of the embodiment shown in FIG. 9—specifically, this figure shows logic for detecting the onset of the signal of interest.

Next, an estimate is made of the onset time for the nerve signal of interest. In the embodiment considered here, this signal is the SNAP signal. The algorithm used to detect the signal onset is shown in FIGS. 9 and 10. Separate searches are used, depending on whether the SA deflection is upward or downward. The search for signal onset is done in a range that extends from a left bound (earliest possible onset) to a right bound (latest possible onset). The left bound is set to be either the baseline peak (if no clipping is present) or the last clipped sample (if clipping is present). The right bound is set based on clinical experience.

When the SA deflection is upward, the procedure first checks for down-peaks that indicate a slope change due to the signal onset. This check is made after low-pass filtering of the signal to reduce noise. If this test does not uncover an onset, a further test is performed that checks for regions where the trace flattens out due to signal onset. The flat region is detected as a first-derivative down-peak followed by a first-derivative up-peak. The amplitude difference between these two peaks is required to exceed a threshold, so that the algorithm will not assign the signal onset based on noise fluctuations.

When the SA deflection is downward, the procedure checks for first-derivative up-peaks that indicate a signal take-off. This estimate of the onset may be refined as indicated in the flowchart of FIG. 9.

In some cases, an independent estimate of the signal onset may be available (for example, the signal onset may be known for another waveform with similar stimulus parameters). In this case, the onset is set to the minimum of (i) the independent onset estimate, and (ii) the onset that is found using the steps illustrated in the flowchart of FIG. 9. This approach ensures that the more conservative estimate will be used in setting the fit region.

Next, the fit region estimated in Section 3A is truncated so that the fit region ends before the signal onset. This ensures that the SA parameters will not be estimated by fitting to data from the nerve signal.

In the next step, a check is made as to whether the onset is within a clipped data region. If the estimated onset is within a clipped region of data, none of the data can be used for fitting the baseline model. An error condition is noted and the routine exits with no SA fit.

Finally, the fit region is adjusted to exclude other clipped data. After these samples are excluded, the resulting fit region may not be contiguous in time. In a small percentage of cases, the result of discarding clipped samples is that very few points are left in the fit region after clipping ends, but a portion of the fit region is left before clipping begins. In these cases, the portion of the fit region before clipping begins is removed completely, in order to avoid fitting a curve to the rising edge of the SA. In a higher percentage of cases, excluding the clipped samples leaves a number of points in the fit region which is less than the number of unknown parameters. In this situation, the fit range is extended after the end of clipping so as to include a number of samples equal to the number of unknowns.

(4) Estimating Parameter Values for the Stimulus Artifact Model

In the preceding procedures (1)-(3), an SA model was developed with a number of unknown parameters (e.g., 2 or 3 parameters for the embodiments described). In addition, a fit region was identified within which the data can be used to estimate the model parameters. A parameter estimation problem must now be addressed. At a high level, this involves calculating a "cost" function that quantifies how well the model fits the data, and providing a numerical method for searching for the best possible fit.

In one embodiment, all model parameters are estimated simultaneously as a multi-parameter estimation problem. In another preferred embodiment, various model parameters are estimated in separate steps. By way of example, and looking now at FIG. 11, the parameters that control the shape of the SA model curves (such as exponential time constants) may be estimated in one step, the amplitude terms may be estimated in another step, etc.

Figure 11:
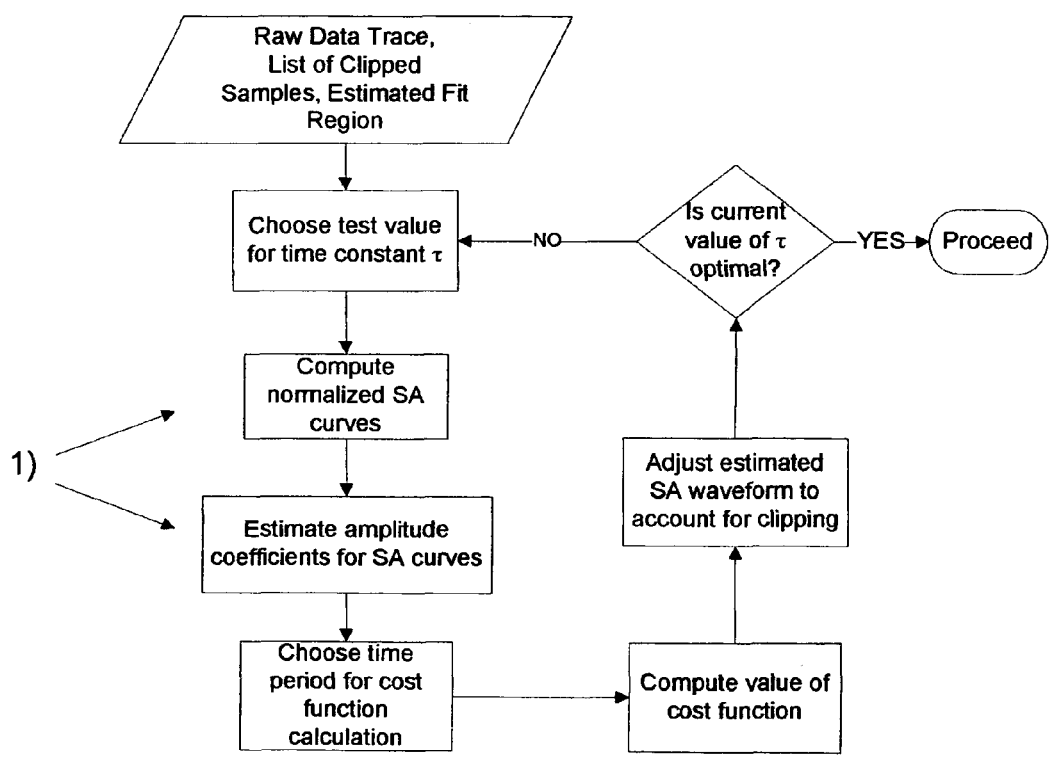
FIG. 11 shows an embodiment of the procedure for estimating the parameters of the stimulus artifact model;.

Note that FIG. 11 involves a search for the best value of an exponential time constant. This search may be embodied in several ways. In one embodiment, the parameter values are discretized within a feasible range of values, and an exhaustive search is made to determine the best possible parameter value. In another embodiment, a search algorithm such as the golden section search, simplex method, or similar algorithm may be used to estimate the parameter value. In still another embodiment, a look-up table may be used in which the characteristics of the SA waveform (such as the SA slope after the SA peak) are compared to tabulated values.

The preferred embodiments of the steps labeled "1)" in FIG. 11 are different for Device A and Device B, so they are discussed separately below.

(4A) Preferred Embodiment When a Single SA Input is Dominant (Device A)

For Device A, the SA model is modeled as the response to a single input waveform, which is a decaying exponential waveform. This decaying exponential waveform is characterized by an amplitude A and time constant $\tau$. Note that for the steps labeled "1)" in FIG. 11, a value of $\tau$ has been assumed.

First, the assumed value of $\tau$ is used to calculate a normalized SA shape from Equation 2. This shape is not yet scaled to match the data in amplitude. It may be denoted:

$$f\_norm(t|\tau).$$

Next, this curve is scaled to match the data in the baseline fit region. In one embodiment, a least-squares solution is used to estimate the scaling factor K which provides the closest match in the fit region. In another embodiment, the scaling factor K is found from:

$$K=\text{median}(\text{data in fit region/baseline shape in fit region}) \quad (9)$$

The resulting modeled SA curve is given by $$f(t|\tau)=K f\_norm(t|\tau) \quad (10)$$

(4B) Preferred Embodiment When Multiple SA Terms Exist (Device B)

As outlined above, two sources of SA exist for Device B: a decaying exponential term, and a voltage offset term. As a first step, unit-amplitude curves corresponding to both of these input terms are calculated using Equations 7 and 8. Note that the DC offset shape is constant, while the decaying exponential term depends on the assumed time constant.

The amplitudes of the two input terms must now be estimated from the data. In one embodiment, this is done using a least squares solution, written in matrix form as:

$$a=D^{-1}x \quad (11)$$

Here, a is a two-element vector containing the estimated amplitudes for the two input waveforms, and x is a vector that contains measured values for the L data samples in the SA fit region. D is a L×2 matrix which contains the SA models. The first column holds the predicted response due to the decaying exponential input for times during the SA fit region. The second column holds the corresponding values for the response to a voltage shift. The exponent of −1 on the matrix denotes the matrix pseudo-inverse. Those skilled in the art will recognize that a variety of standard and well-tested numerical algorithms are available to aid in this least-squares estimation.

Because the two response vectors (columns of D) may be very similar, it is possible that an excellent fit may be obtained in the SA fit region but not elsewhere. Therefore, a preferred embodiment of this procedure uses the least-squares estimate, but imposes an additional constraint, i.e., that the SA model and data should match well at other times in the data recording. This leads to the following algorithm for amplitude estimation:

(i) An unconstrained least-squares solution is found using Equation 11 above.

(ii) The amplitudes from the unconstrained solution are used to generate an estimated SA curve. The values of this curve are compared to the data at a specified time or times in the recording to see if constraints are satisfied. As one example, a constraint may be established so that the modeled SA matches the data to within a specified tolerance:

$$x(T)-\Delta \leq f(T) \leq x(T)+\Delta$$

where x is the signal, f is the model, $\Delta$ is a tolerance in microVolts, and T is a time of interest. Alternatively, instead of using the signal and model values at T, an average of their values in a region about T may be used, or other appropriate constraints may be applied.

(iii) If the constraints are satisfied, the unconstrained solution is accepted.

(iv) If the constraints are violated, additional solutions are attempted which are forced to satisfy the constraints. Thus, in the example above, two additional solutions may be attempted. For the first solution, the SA model f(T) can be constrained to pass through a point $x(T)+\Delta$. For the second solution, the fit is constrained to pass through a point $x(T)-\Delta$. Least-squares solutions are used to find the best solution in the SA fit region subject to these fixed constraints.

(v) Additional solutions are examined. The solution with the minimum "cost" (for example, lowest mean-squared error in the SA fit region) is selected. This solution represents the best possible solution for the given value of $\tau$ that satisfies the constraints.

Figure 12:
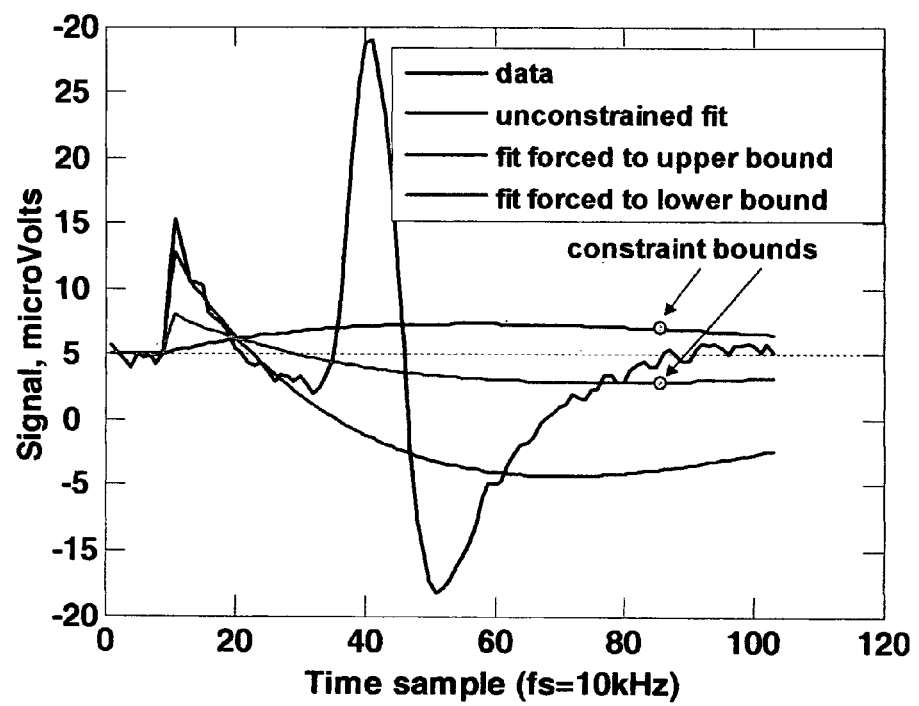
FIG. 12 illustrates the constrained model fitting approach used in an embodiment of the parameter estimation procedure, using data collected with Device B.

This approach is illustrated in FIG. 12. As shown in FIG. 12, the unconstrained least squares solution (green curve) results in a solution which provides a good fit to the data early in time (samples 12-20) where the SA fit region is located. However, the fit is clearly inaccurate later in time.

In this example, a constraint is imposed, i.e., that the data and model should match within 2.5 microVolts of each other at data sample 85 (roughly 8.5 msec). Because the initial fit did not satisfy this constraint, two additional fits that just satisfy the constraint were attempted. The cyan curve which passes through the lower bound provides the lower mean squared error (MSE) and would be selected as the best fit for the assumed value of the time constant. While this particular curve is clearly not a good fit to the data, the constrained fitting approach in this example illustrates how to avoid selection of the unconstrained green curve, which might have led to an erroneous SA fit overall.

(4C) Remaining Steps in Procedure (Same for Device A and Device B)

At this point in the procedure (see FIG. 11), the SA model has been calculated for the assumed value of time constant $\tau$.

The next step is calculating the region of data which will be used to compute the value of the cost function. This region may be referred to as the "cost function region". In a preferred embodiment, the cost function region is initially set to the SA fit region estimated in procedure (3) above.

If clipping is present, the cost function region may be modified as follows:

(i) A check is done to determine whether the absolute value of the SA curve is less than the absolute value of the data in the clipped regions. For these regions, the true curve should be greater than, or equal to, the clipped voltage. Finding a region where the estimated SA curve is less than the clipped value indicates a problem.

(ii) If a problem is detected, the cost function region is extended by adding one sample point which is in the clipped region.

It is important to note that this adjustment applies only to the cost function calculation. Including a single clipped point in the cost function region, when necessary, has been found to be an effective way to achieve accurate numerical fits. The added point increases the "cost" of selecting a fit which underestimates the SA in the clipped region. This added cost causes the numerical solver to converge on solutions which do not underestimate the SA in this region.

Once the cost function region is identified, the difference between the data and model is used to calculate the cost. In a preferred embodiment, the cost is simply the mean squared error in this region. In another embodiment, the mean squared error may be combined with other waveform features which suggest a goodness of fit (see the next procedure for several possibilities).

Finally, the estimated baseline is adjusted to account for clipping away from the baseline region. This is handled by finding the voltage values for which clipping is seen in the data, and then limiting the estimated baseline so that it never exceeds those voltages.

5. Determining Model Goodness-of-Fit

Next, a procedure is provided for determining whether the estimated SA waveform provides a good fit to the data. In this procedure, metrics are calculated that may be used to characterize the goodness of fit. Each metric is compared to a threshold value to determine if the fit is acceptable. In general, multiple metrics should be used to indicate a good fit before the SA model is accepted.

Figure 13:
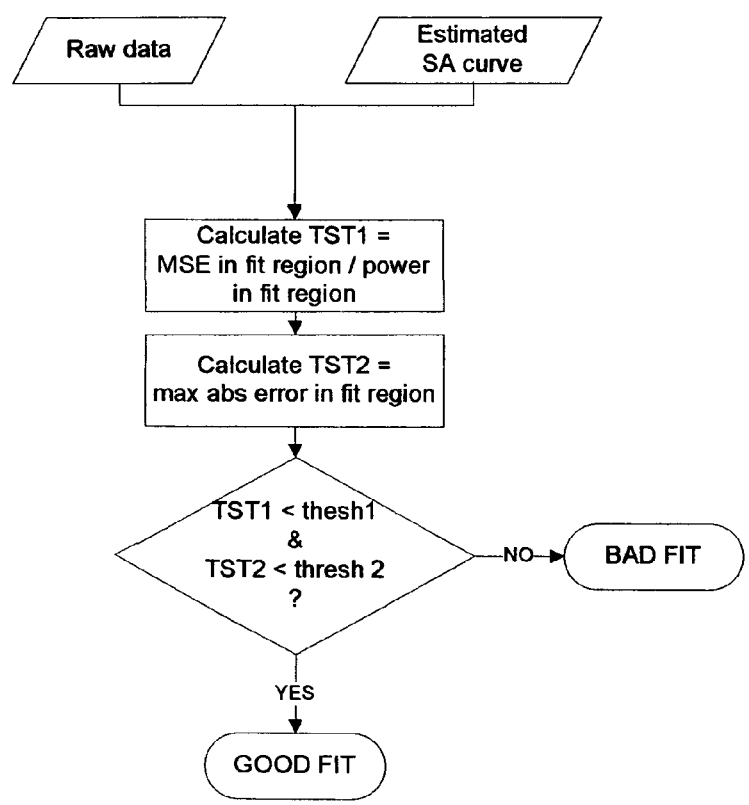
FIG. 13 illustrates an embodiment of the procedure for determining goodness-of-fit.
Figure 14:
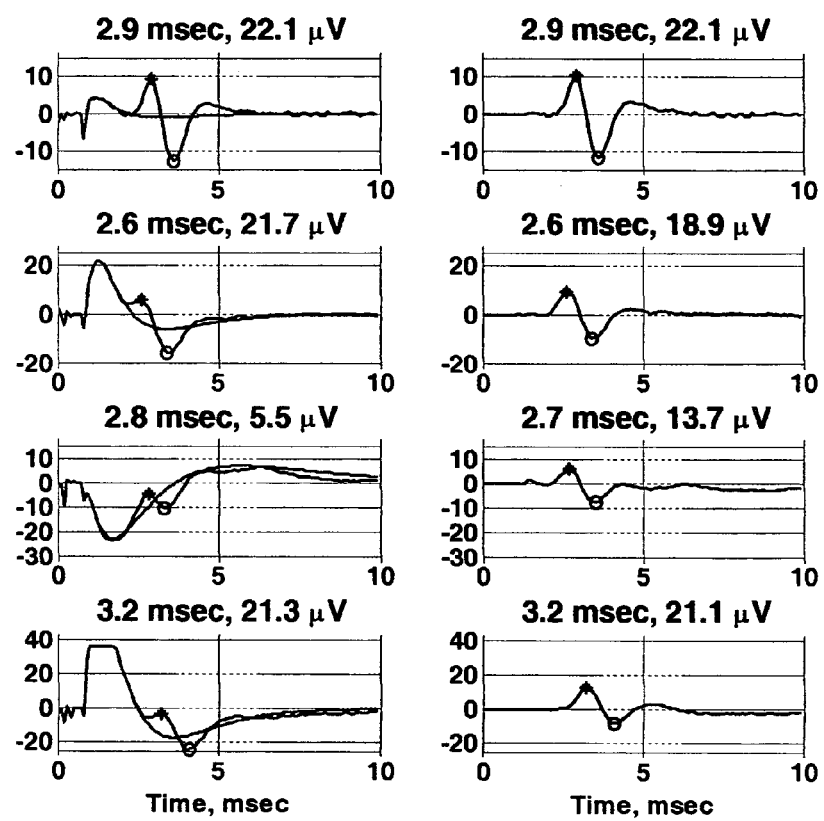
FIG. 14 shows examples of applying the invention to the data acquired using Device A, with the left side showing the raw data and SA fits, and the right side showing the corrected waveforms.
Figure 15:
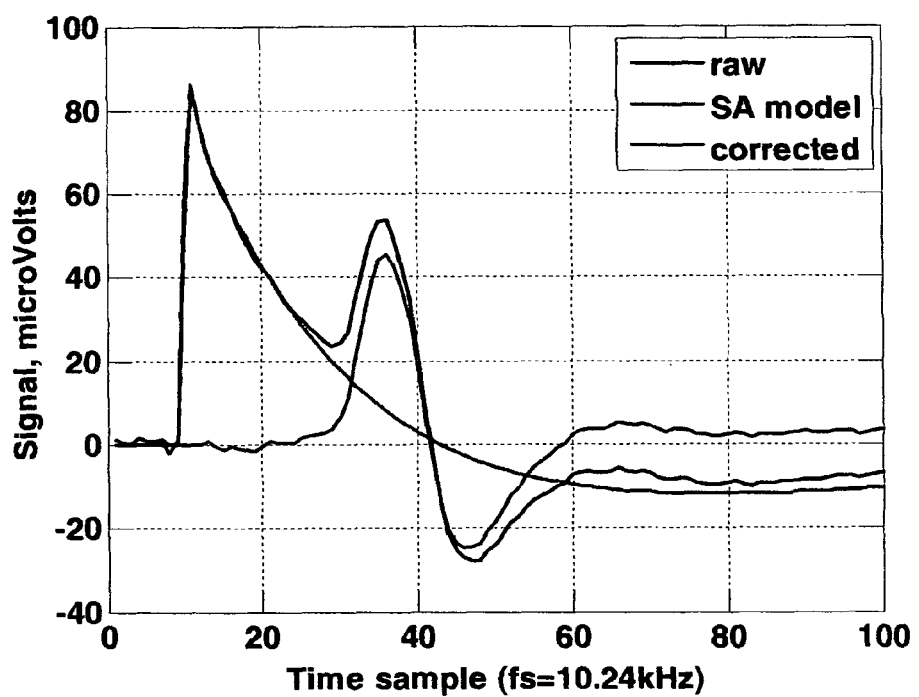
FIG. 15 shows an example of applying the invention to the data acquired using Device B.

FIG. 13 shows a preferred embodiment in which two metrics are used to indicate a good fit. First, the maximum error at a single sample in the fit region should be below a threshold value. Second, the normalized error E in the fit region should be below a threshold $\gamma$. The normalized error E is given by:

$$\varepsilon = \frac{\frac{1}{N}\sum_n (x[n] - f[n])^2}{\frac{1}{N}\sum_n (x[n])^2} \leq \gamma \tag{12}$$

where the data values are x, the SA model is denoted by f, and there are N samples in the SA fit region (note that the sum is only over samples in the SA fit region). The threshold $\gamma$ may be set to a value such as 0.03 (3% error). Normalizing by the power in the fit region gives a way to eliminate the effect of SA amplitude.

The tests shown in FIG. 13 examine how closely the estimated SA waveform tracks the data within the SA fit region. Additional tests may be imposed. For example, if the fit describes all the deterministic behavior of the waveform, the residual errors around the fit should be uncorrelated from sample to sample. If the errors are correlated, there are likely to be unmodeled trends in the data.

Thus, in an alternate embodiment of the method, the SA fit is also required to satisfy statistical tests that seek to detect unmodeled trends in the data. The Durbin-Watson test, and the runs probability test, provide examples of this type of statistical test.

In another embodiment, tests of the goodness-of-fit in the SA fit region may be combined with tests imposed on other portions of the waveform. For example, a constraint may be established so that the SA model and data are reasonably similar late in time, after the signal of interest has passed. In another embodiment, a constraint may be established so that the SA waveform decays to near zero volts near the end of the data record. These types of constraints can help avoid overfitting to the data in the SA fit region.

6. Recovering the Corrected Waveform

After the SA fit is judged to be successful, it is subtracted from the raw data so as to create a corrected waveform:

$$x' = x - f \tag{13}$$

This corrected waveform x' is used for subsequent processing and data display.

7. Combining Artifact Fitting Results Across Multiple Waveforms

The aforementioned procedures (1)-(6) describe the process of estimating and removing SA from a single waveform. In a preferred embodiment of the invention, there is also provided an additional procedure for combining the results of the SA removal process for multiple acquired waveforms. SA removal results can be usefully combined because, in most (although not all) cases, the shape of the SA is relatively constant during a single test as the stimulus current and duration are varied. Depending on the application, the waveforms may represent either averaged or single-trace recordings.

In a first embodiment of this procedure, a requirement may be imposed that SA removal be successful on a number of successive waveforms with similar stimulus parameters. If the algorithm judges that a good fit is achieved on multiple traces, the probability is higher that the SA model accurately describes the data.

In a second embodiment, SA parameter estimates obtained using one waveform may be used when estimating SA parameters for a second waveform. For example, an assumption may be made that the time constant for a decaying exponential will be nearly identical on subsequent waveforms. This may be used to constrain the estimation process.

Note that for some electrode locations, there may be more or less variation in the SA seen in waveforms with similar stimulation parameters. In situations where SA varies noticeably between stimuli, SA removal may be applied before any waveform averaging is carried out. After SA is removed from multiple waveforms, the corrected waveforms are averaged to create data for further analysis.

Modifications

While the present invention has been described in terms of certain exemplary preferred embodiments, it will be readily understood and appreciated by one of ordinary skill in the art that it is not so limited, and that many additions, deletions and modifications to the preferred embodiments may be made without departing from the scope of the present invention.

What is claimed is:

1. A method for the automated removal of a stimulus artifact from a nerve conduction study (NCS) signal waveform acquired from a patient using a single channel NCS system on the basis of a single stimulation, wherein the novel method comprises the steps of:
    (1) developing an analytical model of the stimulus artifact based on known physical properties of the NCS stimulus and known impulse responses of the single channel NCS system;
    (2) using the single channel NCS system to stimulate a nerve and acquire an NCS signal waveform from the patient;
    (3) determining whether stimulus artifact removal should be attempted for the NCS signal waveform, based on the presence of stimulus artifact in the NCS signal waveform;
    (4) identifying a time period which can be used to estimate the model parameters, during which the stimulus artifact is present but no signals of interest are present, whereby to define a fit region within the NCS signal waveform;
    (5) estimating model parameters by numerically fitting the stimulus artifact model to the data within the fit region, wherein the estimation of model parameters comprises numerically fitting the stimulus artifact model to all of the data within the fit region using optimized numerical solvers;
    (6) determining the goodness-of-fit for the modeled stimulus artifact;
    (7) subtracting the modeled stimulus artifact from the NCS signal waveform, including the time period when the signal of interest is present so as to create a corrected waveform; and
    (8) using the corrected waveform to determine nerve conduction characteristics of the patient.

2. A method according to claim 1 wherein the method further comprises the additional step of:
    (9) combining stimulus model fitting results across multiple acquired NCS signal waveforms.

3. A method according to claim 1 wherein the model developed in step (1) is based on one component.

4. A method according to claim 1 wherein the model developed in step (1) is based on at least two components.

5. A method according to claim 3 wherein the model is based on a decaying exponential voltage component.

6. A method according to claim 4 wherein the model is based on a decaying exponential voltage component and a voltage step component.

7. A method according to claim 1 wherein the determination in step (3) comprises comparing (i) the peak amplitude of the NCS signal waveform in a section of the NCS signal waveform likely to contain a stimulus artifact against (ii) a threshold.

8. A method according to claim 1 wherein the identification of a time period and a fit region in step (4) comprises making an initial estimate of the fit region based on the NCS signal waveform features, and then refining the estimate so as to ensure that the fit region does not include any segments where the signal of interest is present, or where the signal of interest is clipped.

9. A method according to claim 8 wherein the identification of the time period and the fit region in step (4) comprises searching for the onset of the signal of interest by using at least one algorithm that searches for an upward- or downward-deflected stimulus artifact.

10. A method according to claim 8 wherein the identification of the time period and the fit region in step (4) comprises searching for the onset of the signal of interest by using a matched filter.

11. A method according to claim 1 wherein the estimation of model parameters in procedure step (4) comprises numerically fitting the stimulus artifact model to the data within the fit region using brute-force numerical solvers.

12. A method according to claim 1 wherein the estimation of model parameters in procedure step (4) comprises numerically fitting the stimulus artifact model to the data within the fit region using look-up table approximations.

13. A method according to claim 1 wherein the estimation of model parameters in step (5) comprises numerically fitting the stimulus artifact model to the data within the fit region and then applying additional constraints to the solution outside the stimulus artifact fit region.

14. A method according to claim 1 wherein the goodness-of-fit determination in step (6) comprises calculating the estimated stimulus artifact waveform and then comparing it to the NCS signal waveform.

15. A method according to claim 14 wherein comparing the estimated stimulus artifact waveform to the NCS signal waveform comprises calculating at least one metric and then comparing that at least one metric to a threshold.

16. A method according to claim 15 wherein the at least one metric comprises the normalized squared error in the stimulus artifact fit region.

17. A method according to claim 15 wherein the at least one metric comprises the worst-case error in the stimulus artifact fit region.

18. A method according to claim 15 wherein the at least one metric comprises a metric such as the Durbin-Watson or "runs" statistic, that seeks to discover correlated trends in the error.

19. A method according to claim 15 wherein the at least one metric comprises constraints on the fit for other portions of the NCS signal waveform.

20. A method according to claim 19 wherein the constraint comprises checking the relationship between the stimulus artifact model and the data at times after the end of the signal of interest.

21. A method according to claim 2 wherein the combining of stimulus model fit results across multiple acquired NCS signal waveforms of step (9) comprises finding good correspondence between the stimulus model and other NCS signal waveforms acquired with similar stimulus parameters.

22. A method for the automated removal of a stimulus artifact from a nerve conduction study (NCS) signal waveform acquired from a patient using a single channel NCS system on the basis of a single stimulation, wherein the method comprises:
   providing an analytical model of the stimulus artifact that is based on known physical properties of the NCS stimulus and known impulse responses of the single channel NCS system;
   using the single channel NCS system to stimulate a nerve and acquire an NCS signal waveform from the patient;
   identifying a time period which can be used to estimate the model parameters, during which the stimulus artifact is present but no signals of interest are present, whereby to define a fit region within the NCS signal waveform;
   fitting the stimulus artifact model to actual NCS data within the fit region within the NCS signal waveform so as to estimate model parameters, wherein the estimation of model parameters comprises numerically fitting the stimulus artifact model to all of the NCS data within the fit region using optimized numerical solvers;
   filtering the stimulus artifact out of the NCS signal waveform using the analytical model so as to create a corrected waveform; and
   using the corrected waveform to determine nerve conduction characteristics of the patient.

23. A method according to claim 22 wherein time periods having clipped data are not present in the fit region.

24. A method according to claim 22 wherein providing the analytical model of the stimulus artifact includes evaluating goodness of fit to determine the accuracy of the model.

25. A method for the automated removal of a stimulus artifact from a nerve conduction study (NCS) signal waveform acquired from a patient using a single channel NCS system on the basis of a single stimulation, wherein the method comprises the steps of:
   (1) developing an analytical model of the stimulus artifact based on known physical properties of the NCS stimulus and known impulse responses of the single channel NCS system;
   (2) using the single channel NCS system to stimulate a nerve and acquire an NCS signal waveform from the patient;
   (3) identifying a time period which can be used to estimate the model parameters, during which the stimulus artifact is present but no signals of interest are present, whereby to define a fit region within the NCS signal waveform;
   (4) estimating model parameters by numerically fitting the stimulus artifact model to the data within the fit region, wherein the estimation of model parameters comprises numerically fitting the stimulus artifact model to all of the data within the fit region using optimized numerical solvers;
   (5) determining the goodness-of-fit for the modeled stimulus artifact;
   (6) subtracting the modeled stimulus artifact from the NCS signal waveform, including the time period when the signal of interest is present so as to create a corrected waveform; and
   (7) using the corrected waveform to determine nerve conduction characteristics of the patient.

26. A method for the automated removal of a stimulus artifact from an electrophysiological signal waveform acquired from a patient using a single channel electrophysiological measurement system on the basis of a single stimulation, wherein the method comprises the steps of:
   (1) developing an analytical model of the stimulus artifact based on known physical properties of the electrophysiological stimulus and known impulse responses of the single channel electrophysiological measurement system;
   (2) using the single channel electrophysiological measurement system to stimulate a nerve and acquire an electrophysiological signal waveform from the patient;
   (3) identifying a time period which can be used to estimate the model parameters, during which the stimulus artifact is present but no signals of interest are present, whereby to define a fit region within the electrophysiological signal waveform;
   (4) estimating model parameters by numerically fitting the stimulus artifact model to the data within the fit region, wherein the estimation of model parameters comprises numerically fitting the stimulus artifact model to all of the data within the fit region using optimized numerical solvers;
   (5) determining the goodness-of-fit for the modeled stimulus artifact;
   (6) subtracting the modeled stimulus artifact from the electrophysiological signal waveform, including the time period when the signal of interest is present so as to create a corrected waveform; and
   (7) using the corrected waveform to determine electrophysiological response characteristics of the patient.

27. A method for the automated removal of a stimulus artifact from an electrophysiological signal waveform acquired from a patient using a single channel electrophysiological measurement system on the basis of a single stimulation, wherein the method comprises:

providing an analytical model of the stimulus artifact that is based on known physical properties of the electrophysiological stimulus and known impulse responses of the single channel electrophysiological measurement system;

using the single channel electrophysiological measurement system to stimulate a nerve and acquire an electrophysiological signal waveform from the patient;

identifying a time period which can be used to estimate the model parameters, during which the stimulus artifact is present but no signals of interest are present, whereby to define a fit region within the electrophysiological signal waveform;

fitting the stimulus artifact model to actual electrophysiological data within the fit region within the electrophysiological signal waveform so as to estimate model parameters, wherein the estimation of model parameters comprises numerically fitting the stimulus artifact model to all of the electrophysiological data within the fit region using optimized numerical solvers;

filtering the stimulus artifact out of the electrophysiological signal waveform using the analytical model so as to create a corrected waveform; and using the corrected waveform to determine electrophysiological response characteristics of the patient.

28. Apparatus for the automated removal of a stimulus artifact from an electrophysiological signal waveform acquired from a patient using a single channel electrophysiological measurement system on the basis of a single stimulation, wherein the apparatus is configured to:

(1) store an analytical model of the stimulus artifact based on known physical properties of the electrophysiological stimulus and known impulse responses of the single channel electrophysiological measurement system;

(2) identify a time period which can be used to estimate the model parameters, during which the stimulus artifact is present but no signals of interest are present, whereby to define a fit region within the electrophysiological signal waveform;

(3) estimate model parameters by numerically fitting the stimulus artifact model to the data within the fit region, wherein the estimation of model parameters comprises numerically fitting the stimulus artifact model to all of the data within the fit region using optimized numerical solvers;

(4) determine the goodness-of-fit for the modeled stimulus artifact; and (5) subtract the modeled stimulus artifact from the electrophysiological signal waveform, including the time period when the signal of interest is present so as to create a corrected waveform.

29. Apparatus for the automated removal of a stimulus artifact from an electrophysiological signal waveform acquired from a patient using a single channel electrophysiological measurement system on the basis of a single stimulation, wherein the apparatus is configured to:

store an analytical model of the stimulus artifact that is based on known physical properties of the electrophysiological stimulus and known impulse responses of the single channel electrophysiological measurement system;

identify a time period which can be used to estimate the model parameters, during which the stimulus artifact is present but no signals of interest are present, whereby to define a fit region within the electrophysiological signal waveform;

fit the stimulus artifact model to actual electrophysiological data within a fit region within the electrophysiological signal waveform so as to estimate model parameters, wherein the estimation of model parameters comprises numerically fitting the stimulus artifact model to all of the electrophysiological data within the fit region using optimized numerical solvers; and filter the stimulus artifact out of the electrophysiological signal waveform using the analytical model so as to create a corrected waveform.

\* \* \* \* \*